United States Patent [19]

Buchhorn et al.

[11] Patent Number: 4,919,666
[45] Date of Patent: Apr. 24, 1990

[54] IMPLANT HAVING RECESSES FOR THERAPEUTICALLY EFFECTIVE SUBSTANCES

[75] Inventors: Ursula Buchhorn; Hans B. Willert, both of Göttingen, Fed. Rep. of Germany

[73] Assignee: Sulzer Brothers Limited, Winterthur, Switzerland

[21] Appl. No.: 284,094

[22] Filed: Dec. 14, 1988

Related U.S. Application Data

[63] Continuation of Ser. No. 40,929, Apr. 21, 1987, abandoned.

[30] Foreign Application Priority Data

May 5, 1986 [CH] Switzerland .................... 01834/86

[51] Int. Cl.$^5$ ............................ A61F 2/28; A61F 5/04
[52] U.S. Cl. ......................................... 623/16; 606/62; 606/76

[58] Field of Search ................. 623/11, 12, 16, 18, 623/19, 20, 21, 22, 23; 128/92 Y, 92 YZ, 92 YQ, 92 YP

[56] References Cited

U.S. PATENT DOCUMENTS 3,993,072 11/1976 Zaffaroni ........................ 623/16
4,375,810 3/1983 Belykh et al. .................. 623/16

Primary Examiner—David J. Isabella
Attorney, Agent, or Firm—Kenyon & Kenyon

[57] ABSTRACT

The implant is provided with recesses in which therapeutically effective substances are embedded. Each recess is closed by a porous cover which is of a porosity to permit permeation of the therapeutic substance out of the recess while preventing ingrowth of bone tissue. Each cover may be slightly deformed into a convex shape to project from a recess to achieve elastic bonding with a bone.

14 Claims, 4 Drawing Sheets

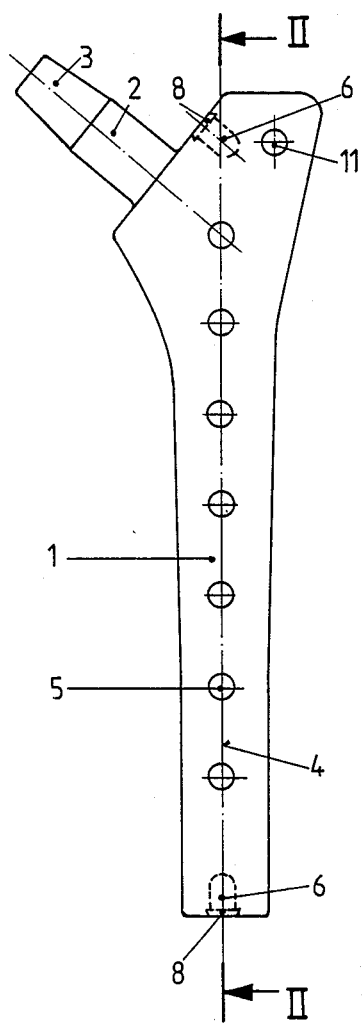

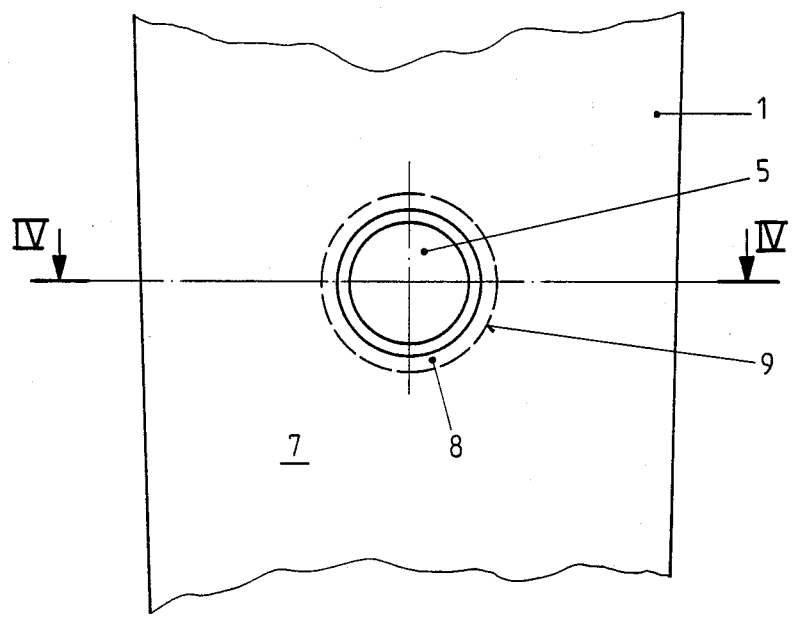
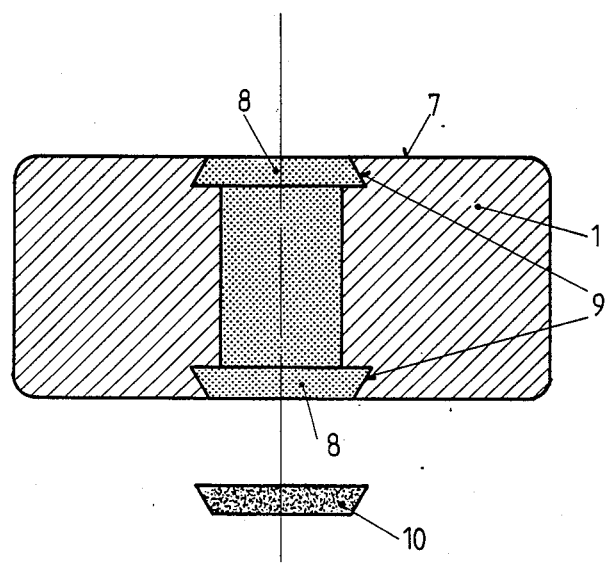

IMPLANT HAVING RECESSES FOR THERAPEUTICALLY EFFECTIVE SUBSTANCES

This is a continuation of application Ser. No. 040,929 filed Apr. 21, 1987 now abandoned.

This invention relates to an implant having recesses for therapeutically effective substances.

Heretofore, it has been known, for example as described in German O.S.2839040, to provide surfaces of implants which border on tissue with depressions or recesses in which therapeutically effective substances can be embedded. Such substances may, for example, be antibiotica or other anti-inflammatory agents, anticoagulants as well as substances for stimulating and supporting tissue growth. Generally, the therapeutica substance is released by being dissolved in body fluids which then transport the therapeutic substances to the live tissue.

However, in cases where the implants have been provided with "hollow" recesses, ingrowth of tissue into the recesses also takes place. Generally, such ingrowth of tissue is neither permissible nor desirable, for example in those cases where it has been surgically difficult to approach areas of an implant anchoring site. Further, in those cases where anchoring of an implant is caused by a conical clamping, for example via a conical shaft of a joint endoprosthesis, re-setting of the implant by further penetration into a bone can be prevented by the ingrown tissue.

Accordingly, it is an object of the invention to prevent the ingrowth of tissue into the recesses of an implant provided for therapeutically effective substances.

It is another object of the invention to impede tissue growth into the recesses of an implant containing a therapeutically effective substance.

Briefly, the invention is directed to an implant which has an implantable body having at least one recess in a surface thereof which is sized to receive a therapeutically effective substance for subsequent release into surrounding tissue. In accordance with the invention, a porous cover is secured in the body to close over the recess. In this respect, the cover has a porosity which is sufficient to be permeable to the substance received in the recess and to fluids having the substance dissolved therein while being impermeable to the ingrowth of tissue.

The porosity of the cover is such that the pores of the cover are of a pore size of no more than 50 μm. Such a pore size greatly inhibits the ingrowth of bone while at the same time permitting free passage of body fluids and the therapeutically effective substances. The lower limit of the pore size in this connection is a function of the size of the molecules of the therapeutic substance to be transported.

The concentration of the therapeutic substance and the duration of its release can be regulated through the solubility and/or the degradation of salivary substance. For particular infections, a specific substance combination can be prepared in accordance with an antibiogram. Since the implant is anchored in a cement-free manner, the heat stability of the therapeutic substance need not be taken into account since there is no exothermic polymerizing bone cement used.

After adequate structural stability is ensured, the number, size and distribution of the recesses in the implant body depend on therapeutic considerations, for example on the concentration needed outside the implant and/or the site on which the substance acts and space requirements for the therapeutic substances.

Advantageously, the porous cover is made of elastic material and is clamped in the recess under a prestress. In this connection, an additional advantage is provided if the clamped cover is deformed into a convex shape directed outwardly of the body in order to achieve an elastic bonding with the bone.

In a case of rod-like or blade-like anchoring parts, for example with the blade-like shaft of a prosthesis for the head of a femur, the recess may be formed as a perforation bore which passes completely through the anchoring part. In this case, a porous cover is provided at each end of the bore.

Each porous cover may also be sized so that the outside surface merges into the surface of the implant body since this prevents or, at least, impedes tissue growth between the cover and the implant.

The recesses for the therapeutic substances may be located on any suitable anchoring part, for example, on femur shafts or convex surfaces of hip joint acetabular as well as on other constructive elements such as in the collar or neck region of a prosthesis for the head of a femur, the sides of a tibia plateau and/or condylar glide surfaces. The cross sections of the recesses may also be of any suitable shape. From the manufacturing point of view, simple shapes are desirable, such as circular cross-sectional shapes.

The porous covers may be made of any suitable material for implant purposes. For example, the covers may be made of porous synthetic materials such as polyethylene or porous metals, for example a wire mesh or sintered materials of tissue-compatible material such as titanium or titanium alloys.

In order to secure a cover over a recess, various techniques may be used. For example, a groove may be provided in the implantable body coaxial of the recess with a conical wall so as to form a conical undercut. In this embodiment the cover is disposed in the groove and has a conical periphery which mates with the conical wall of the groove. In this case, the use of a cover made of elastic material is particularly suitable. In other cases, a rectangular groove can be placed in alignment with a recess below the surface of the implant with the cover clamped within the groove. Further, both the recess and a cover may be provided with threads so that the cover can be threaded into the recess.

It is also possible to enlarge a recess with a groove for receiving a cover at the outer surface of the implant with the groove having threads in a side wall. In this case, the outer diameter of the cover would be adapted to the enlarged groove and provided with external threads. If the cover is made of an elastic material, the cover can additionally be fixed while being clamped by deformation during threading into the groove.

These and other objects and advantages of the invention will become more apparent from the following detailed description taken in conjunction with the accompanying drawings wherein:

FIG. 1 illustrates a schematic side view anterior/-posterior of a straight shaft of a prosthesis for the head of a femur;

FIG. 2 illustrates a view taken on line II—II of FIG. 1;

FIG. 3 illustrates an enlarged view of a recess in the prosthesis of FIG. 1;

FIG. 4 illustrates an exploded view taken on line IV—IV on FIG. 3;

Figure 5:
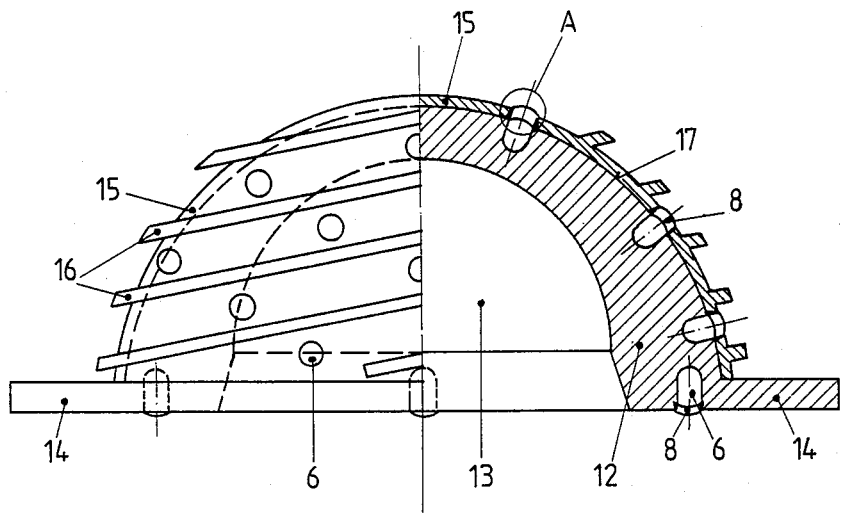
FIG. 5 illustrates a part cross-sectional view of an acetabulum constructed in accordance with the invention.

Referring to FIGS. 1 and 2, the prosthesis for the head of a femur includes a blade-like straight shaft 1 which widens conically from the distal end to the proximal end and carries a prosthesis neck 2 at the proximal end. In addition, a peg 3 is located on the neck 2 for receiving a joint head (not shown). As indicated, the shaft 1 has a longitudinal center axis 4 along which a large number of recesses are provided for embedding of therapeutically effective substances therein. These recesses constitute a plurality of perforation bores 5 which pass completely through the shaft 1 and pockets 6, one of which is located at the distal and a second of which is located at the proximal end adjacent to the neck 2.

Referring to FIGS. 3 and 4, each perforation bore 5 is enlarged at each side surface 7 of the shaft 1 by means of a punched groove 8 having an undercut 9. As indicated, each groove has a conical wall for forming the undercut 9. In addition, each groove 8 receives a porous cover 10 of elastic material, such as polyethylene. Further, each cover 10 has a conical periphery which mates with the conical wall of an enlarged groove 8 so as to be firmly secured in place. Further, the diameter of the cover 10 is slightly larger than the groove 8 so that the conicity of the groove 8 supports a slight convex shape of the cover 10 and insures permanent tension with a secure permanent clamping of the cover 10 against the shearing forces which occur, for example during implantation.

Each perforation bore 5 when closed by a cover 10 at each end forms a chamber for holding therapeutically effective substances.

As indicated in FIG. 1, each pocket 6 also has an enlarged groove 8 at the entrance for receiving a porous cover as above. Further, such pockets may also may be placed where a cross-section of the implant is small and/or for the purpose of the specific local arrangement.

As indicated in FIG. 1, an additional bore 11 is provided in the proximal end of the shaft which widens in wing-like fashion towards the trochanter major. This bore 11 provides an application point for a removal instrument should it be necessary to repeat a surgical procedure.

Referring to FIG. 5, the implant may be in the form of an acetabular prosthesis, for example of two-part construction, for a hip joint. In this embodiment, the acetabular prosthesis includes an acetabular body 12 of synthetic material having a cavity or bowl 13 for receiving a joint head (not shown), a circumferential base 14 about the cavity 13 which extends in flange-like manner and a hemispherical outer surface 17. In addition, a plurality of pockets 6 are distributed in a hemispherical outer surface 17 for receiving therapeutically effective substances.

Figure 6:
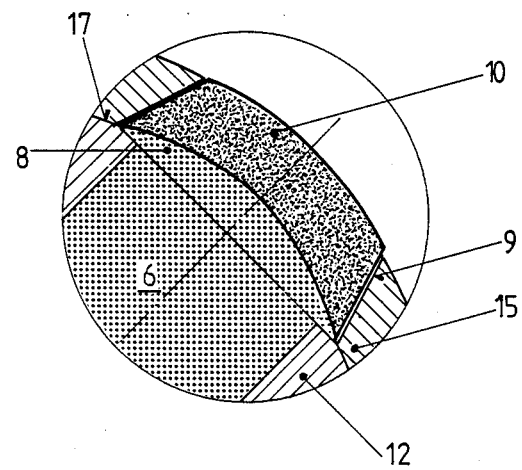
FIG. 6 illustrates an enlarged detail view of a porous cover of FIG. 5.

The acetabular prosthesis also includes a hemispherical bowl 15, for example of metal, which is mounted over the hemispherical surface 17 of the body 12. The bowl 15 may be formed, for example of titanium, a titanium alloy, or other tissue-compatible metalic materials. In addition, the bowl 15 is provided with suitable means such as screw threads 16 for anchoring the prosthesis in a pelvic bone. In addition, the bowl 15 is provided with a plurality of openings 8 each of which is aligned with and which communicates with a pocket 6. Each opening 8 is also provided with a conical wall to form an undercut 9 as indicated in FIG. 6. As such, each opening 8 receives and retains a porous cover 10 in order to close the respective pocket 6.

Similar pockets 6 may also be provided in the base of the acetabular body 12 with porous covers closing each pocket 6.

While the pockets 6 in the outer surface 17 of the acetabular body 12 supply therapeutically active substances to the tissue adjacent to the implant, the pockets 6 in the base 14 of the acetabular body 12 supply therapeutically active agent into the inner joint space in a manner similar to those on the contact surface for a prosthesis neck 2 in the embodiment of FIGS. 1 and 2.

Referring to FIG. 6, the diameter of clamped cover 10 is selected relative to that of the opening 8 so that the clamped cover 10 exhibits a decided convex shape toward the outside. In this way, when implanted, a cover 10 rests against the bone while also being supported in place.

Figure 7:
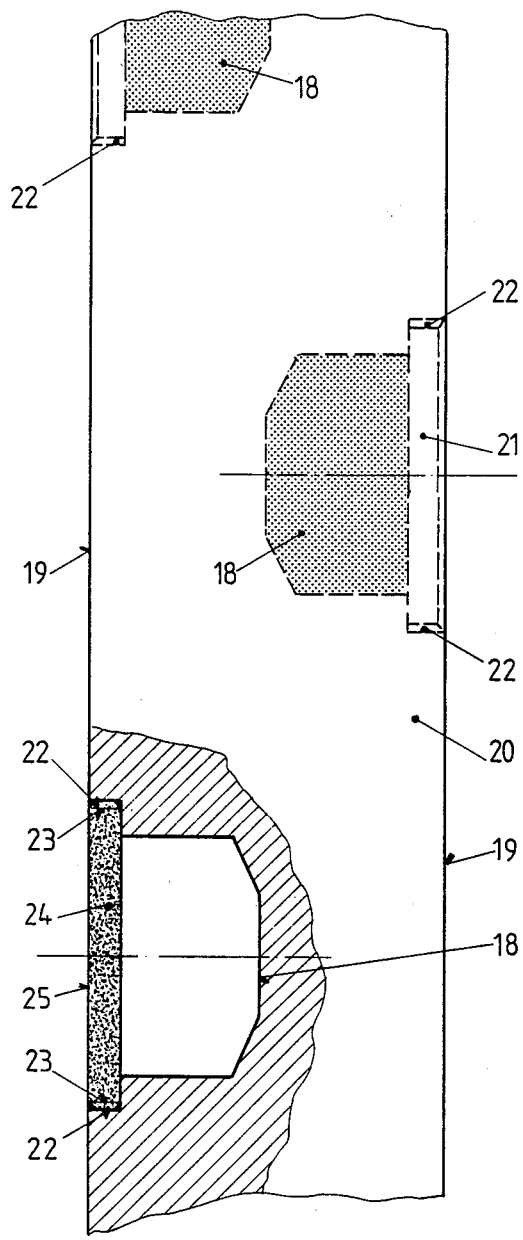
FIG. 7 illustrates a modified anchoring part of an implant constructed in accordance with the invention.

If the desired solidity of an implant does not permit perforation bores such as those shown in FIGS. 1 and 2, the possibility exists of placing recesses even in small implant elements by distributing pockets 18 in a staggered fashion, for example as indicated in FIG. 7. In this case, the pockets 18 are preferentially arranged outside the principal stress directions. Further, each pocket can be widened at the surface 19 of the implant 20 into a groove 21 with threads 22 being provided on the cylindrical wall of the groove 21. In this case, a porous cover can be provided with external threads 23 for threading into the groove 21.

In order to impede tissue growth between a cover 24 and the implant surface 19 or to prevent ingrowth altogether, the outer surface 25 of each cover 24 may merge into the implant surface 19 as smoothly as possible.

The invention thus provides a relatively simple means for preventing the ingrowth of bone tissue into recesses of an implant containing therapeutically effective substances. Further, the invention provides a cover for a recess containing a therapeutic agent or substance which permits passage of the substance into the bone tissue while preventing passage of the bone tissue into the recess.

What is claimed is:

1. A bone implant for insertion into a bone cavity comprising a body configured for implanting into a bone cavity and having at least one recess in a surface thereof, said recess being sized to receive a therapeutically effective substance for subsequent release into surrounding tissue in said cavity; and a separate porous cover separately secured in said body from the therapeutically effective substance to close over said recess, said cover having a porosity sufficient to be permeable to the substance received in said recess and to fluids having the substance dissolved therein while being impermeable to the ingrowth of bone tissue.

2. An implant as set forth in claim 1 wherein said cover has pores of a pore size of no more than 50 μm.

3. An implant as set forth in claim 1 wherein said cover is deformed into a convex shape outwardly of said body to clampingly engage said recess.

4. An implant as set forth in claim 1 wherein said body is an anchoring shaft of a prosthesis and said recess extends through said shaft and which includes a pair of said covers, each said cover being disposed at a respective end of said recess.

5. An implant as set forth in claim 1 wherein said cover has a surface merging into said surface of said body to impede tissue ingrowth therebetween.

6. An implant as set forth in claim 1 wherein said body includes a groove coaxial of said recess and having a conical wall and said cover is disposed in said groove and has a conical periphery mating with said conical wall.

7. A prosthesis comprising
a body having an anchoring shaft configured for implanting into a bone cavity with at least one recess in a surface thereof, said recess being sized to receive a therapeutically effective substance for subsequent release into surrounding tissue; and
a porous cover separately secured in said body to close over said recess from the therapeutically effective substance, said cover having a porosity sufficient to be permeable to the substance received in said recess and to fluids having the substance dissolved therein while being impermeable to the ingrowth of bone tissue.

8. A prosthesis as set forth in claim 7 having a plurality of said recesses therein and a plurality of said covers, each said cover being disposed to close at least one end of a respective recess.

9. An acetabular prosthesis comprising
an acetabular body having a cavity for receiving a joint head, a circumferential base about said cavity, an outer hemispherical surface, at least one pocket in said surface for receiving a therapeutic effective substance;
a hemispherical bowl mounted over said surface and having at least one opening aligned with and communicating with said pocket; and
a porous cover in said opening of said bowl to close said pocket, said cover having a porosity sufficient to be permeable to the substance received in said pocket while being impermeable to an ingrowth of tissue.

10. An acetabular prosthesis as set forth in claim 9 which further includes at least one pocket in said base to receive a therapeutically effective substance and a porous cover closing said pocket in said base and having a porosity sufficient to be permeable to the substance received in said pocket while being impermeable to an ingrowth of tissue.

11. An implant comprising
an implantable body having at least one recess in a surface thereof, said recess being sized to receive a therapeutically effective substance for subsequent release into surrounding tissue; and
a porous cover made of elastic material which is prestressed to clamp said cover in said recess of said body to close over said recess, said cover having a porosity sufficient to be permeable to the substance received in said recess and to fluids having the substance dissolved therein while being impermeable to the ingrowth of tissue.

12. A prosthesis comprising
a body having an anchoring shaft with a plurality of recesses in a surface thereof, each said recess being sized to receive a therapeutically effective substance for subsequent release into surrounding tissue; and
a plurality of porous covers, each said porous cover being separately secured in said body to close over a respective recess from the therapeutically effective substance, each said cover having a porosity sufficient to be permeable to the substance received in a respective recess and to fluids having the substance dissolved therein while being impermeable to the ingrowth of tissue and being made of elastic material which is prestressed to clamp said cover in a respective recess.

13. A prosthesis as set forth in claim 12 wherein each cover is deformed into a convex shape outwardly of said shaft to clampingly engage said recess.

14. A prosthesis comprising
a body having an anchoring shaft with at least one recess in a surface thereof and a groove coaxial about said recess and having a conical wall, said recess being sized to receive a therapeutically effective substance for subsequent release into surrounding tissue; and
a porous cover separately secured in said groove of said body to close over said recess from the therapeutically effective substance, said cover having a conical periphery mating with said conical wall and a porosity sufficient to be permeable to the substance received in said recess and to fluids having the substance dissolved therein while being impermeable to the ingrowth of tissue.

* * * * *

UNITED STATES PATENT AND TRADEMARK OFFICE
CERTIFICATE OF CORRECTION

PATENT NO. : 4,919,666
DATED : April 24, 1990
INVENTOR(S) : URSULA BUCHHORN, et al It is certified that error appears in the above-identified patent and that said Letters Patent is hereby corrected as shown below:

Column 1, line 16 "therapeutica" should be -therapeutic-
Column 4, line 66 "1" should be -11-

Signed and Sealed this

Fifteenth Day of October, 1991

Attest:

HARRY F. MANBECK, JR.

*Attesting Officer*     *Commissioner of Patents and Trademarks*